United States Patent
Bell et al.

(10) Patent No.: US 10,584,233 B2
(45) Date of Patent: Mar. 10, 2020

(54) FLOWABLE BULK GRANULAR POLYSACCHARIDE

(71) Applicant: E I DU PONT DE NEMOURS AND COMPANY, Wilmington, DE (US)

(72) Inventors: Timothy Allan Bell, Wilmington, DE (US); Dean M. Fake, Wilmington, DE (US); Scott M. Herkimer, Wilmington, DE (US); Dhiren V. Patel, Hockessin, DE (US); Tyler D. Pritchett, Bear, DE (US)

(73) Assignee: DUPONT INDUSTRIAL BIOSCIENCES USA, LLC, Wilmington, DE (US)

( * ) Notice: Subject to any disclaimer, the term of this patent is extended or adjusted under 35 U.S.C. 154(b) by 0 days.

(21) Appl. No.: 16/158,327

(22) Filed: Oct. 12, 2018

(65) Prior Publication Data
US 2019/0112456 A1 Apr. 18, 2019

Related U.S. Application Data

(60) Provisional application No. 62/725,532, filed on Aug. 31, 2018, provisional application No. 62/571,995, filed on Oct. 13, 2017.

(51) Int. Cl.
*C08L 5/00* (2006.01)
*C08B 37/00* (2006.01)
*C12P 19/04* (2006.01)
*C12P 19/18* (2006.01)

(52) U.S. Cl.
CPC ............ *C08L 5/00* (2013.01); *C08B 37/0009* (2013.01); *C12P 19/04* (2013.01); *C12P 19/18* (2013.01)

(58) Field of Classification Search
CPC .. C08L 5/00; C12P 19/04; C12P 19/18; C08B 37/009
See application file for complete search history.

(56) References Cited

U.S. PATENT DOCUMENTS

| | | | |
|---|---|---|---|
| 5,705,184 A * | 1/1998 | Donzis | A61K 31/715 424/442 |
| 5,952,205 A | 9/1999 | Catani et al. | |
| 6,242,225 B1 | 6/2001 | Catani et al. | |
| 6,660,502 B2 | 12/2003 | Catani et al. | |
| 6,867,026 B2 | 3/2005 | Van Geel-Schutten et al. | |
| 7,000,000 B1 | 2/2006 | O'Brien | |
| 7,670,811 B2 | 3/2010 | Vercauteren et al. | |
| 8,642,757 B2 | 2/2014 | O'Brien et al. | |
| 8,871,474 B2 | 10/2014 | Payne et al. | |
| 9,644,322 B2 | 5/2017 | Massouda | |
| 2003/0153746 A1 | 8/2003 | Van Lengerich et al. | |
| 2005/0249853 A1 | 11/2005 | Merrill et al. | |
| 2013/0157316 A1 | 6/2013 | Caimi et al. | |
| 2013/0196384 A1 | 8/2013 | Caimi et al. | |
| 2013/0244287 A1 | 9/2013 | O'Brien et al. | |
| 2013/0244288 A1 | 9/2013 | O'Brien et al. | |
| 2014/0087431 A1 | 3/2014 | Payne et al. | |
| 2014/0179913 A1 | 6/2014 | Paullin et al. | |
| 2015/0167243 A1 | 6/2015 | Bilodeau et al. | |
| 2015/0232819 A1 | 8/2015 | Paullin et al. | |
| 2015/0240278 A1 | 8/2015 | Nagy et al. | |
| 2015/0240279 A1 | 8/2015 | Nagy et al. | |
| 2015/0275256 A1 | 10/2015 | Fake et al. | |
| 2016/0002693 A1 | 1/2016 | Caimi et al. | |
| 2016/0230348 A1 * | 8/2016 | Massouda | D21J 3/12 |
| 2016/0304629 A1 | 10/2016 | Kasat et al. | |
| 2016/0311935 A1 | 10/2016 | Dennes et al. | |
| 2017/0002335 A1 | 1/2017 | Payne et al. | |
| 2017/0002336 A1 | 1/2017 | Payne et al. | |
| 2017/0166938 A1 | 6/2017 | Nagy et al. | |
| 2017/0204203 A1 | 7/2017 | Massouda et al. | |
| 2017/0208823 A1 | 7/2017 | Massouda et al. | |
| 2018/0021238 A1 | 1/2018 | Huh et al. | |
| 2018/0072998 A1 | 3/2018 | Li et al. | |
| 2019/0218373 A1 | 7/2019 | Opietnik et al. | |

FOREIGN PATENT DOCUMENTS

| | | |
|---|---|---|
| WO | 2014/099724 A1 | 6/2014 |
| WO | 2015200590 A1 | 12/2015 |
| WO | 2016/126685 A1 | 8/2016 |
| WO | 2016126685 A1 | 8/2016 |
| WO | 2017079595 A1 | 5/2017 |

OTHER PUBLICATIONS

International Search Report and Written Opinion—PCT/US2018/055573—dated Jan. 2, 2019.
Simpson et al., Four Glucosyltransferases, GTFJ, GTFK, GTFL, and GTFM, From *Streptococcus salivarius* ATCC 25975, Microbiology, vol. 141 (1995), pp. 1451-1460.
Cantarel et al., The Carbohydrate-Active Enzymes Database (CAZY): An Expert Resource for Glycogenomics, Nucleic Acids Research, vol. 37 (2009), Database Issued, pp. 233-238.
Rogers, Chapter 5: The Molecular Biology of Cariogenic Bacteria, From Molecular Biology, Horizon Scientific Press, Roy RB Russell (2008), pp. 120-122.
Komatsu et al., Kinetics of Dextran-Independent α-(1→3)-Glucan Synthesis by Strepto-Coccus Sobrinus Glucosyltransferase I, FEBS J., vol. 278 (2011), pp. 531-540.

(Continued)

*Primary Examiner* — Carlos A Azpuru

(57) ABSTRACT

Disclosed herein are compositions comprising polysaccharide particles with an average size of about 0.1-10 mm. These particles comprise at least (i) about 50%-90% by weight water or an aqueous solution, and (ii) about 10%-50% by weight insoluble alpha-glucan, or an insoluble cationic ether thereof, comprising alpha-1,3-glycosidic linkages and having a weight-average degree of polymerization (DPw) of at least about 100. Further disclosed are methods of preparing these compositions, as well as systems for storing and/or moving them.

19 Claims, No Drawings

(56) References Cited

OTHER PUBLICATIONS

Eifuku et al., Production and Partial Characterization of the Extra-Cellular Polysaccharides From Oral *Streptococcus salivarius*, Carbohydrate Research, vol. 194 (1999), pp. 247-260.

Goffin et al., A Systematic NMR Determination of α-D-Glucooligosaccharides, Effect of Linkage Type, Anomeric Configuration and Combination of Different Linkages Type on 13C Chemical Shifts for the Determination of Unknown Isomaltooligosaccharides, Bull. Korean Chem. Soc., vol. 30, (2009), pp. 2535-2541.

Kingston et al., Role of the C-Terminal YG Repeats of the Primer-Dependent Streptococcal Glucosyltransferase, GTFJ, in Binding to Dextran and Mutan, Microbiology, vol. 148 (2002), pp. 549-558.

Konishi et al., Structure and Enzymatic Properties of Genetically Truncated Forms of the Water-Insoluble Glucan-Synthesizing Glucosyltransferase From *Streptococcus sobrinus*, J. Biochem., vol. 126 (1999), pp. 287-295.

Leemhuis et al., Glucansucrases: Three-Dimensional Structures, Reactions, Mechanism, α-Glucan Analysis and Their Implications in Biotechnology and Food Applications, Journal of Biotechnology, vol. 163 (2013), pp. 250-272.

Monchois et al., Isolation of an Active Catalytic Core of *Streptococcus downei* MFE28 GTF-I Glucosyltransferase, Journal of Bacteriology, vol. 181, No. 7 (1999), pp. 2290-2292.

Monchois et al., Glucansucrases: Mechanism of Action and Structure-Function Relationships, FEMS Microbiology Reviews, vol. 23 (1999), pp. 131-151.

Jenike, "Storage and Flow of Solids", Bulletin of the U. of Utah, Bulletin No. 123, vol. 53, No. 26 (1964).

ASTM Int'l, "Standard Test Method for Shear Testing of Bulk Solids Using the Jenike Shear Tester", D6128-16 (2017).

ASTM Int'l, "Standard Test Method for Bulk Solids Using Schulze Ring Shear Tester", D6773-16 (2017).

Bell, et al. "Practical Evaluation of the Johanson Hang-Up Indicizer", Bulk Solids Handling, 14(1), pp. 117-125 (1994).

Van Der Kraan, et al., "3rd European Symposium—Storage and Flow of Particulate Solids", Janssen Centennial, Proc. of PARTEC 95, Nuremberg, pp. 57-68 (1995).

Juarez-Enriquez, et al., "Effect of water content on the flowability of hygroscopic powders", J.Food Engineering, vol. 205 pp. 12-17 (2017).

Giffard, et al., "Molecular characterization of a cluster of at least two glucosyltransferase genes in *Streptococcus salivarius* ATCC 25975", J. Gen. Micro., vol. 137, pp. 2577-2593 (1991).

Lenges, "DuPont BioMaterials: Enzymatic polymerization—A new process for engineered polysaccharides", Biobased Performance Materials Symposium, Wageningen, The Netherlands (2017).

Wang et al., "Synthesis of quaternary (1 → 3)-alpha-D-glucan and its antibacterial activity", J. Beijing U., vol. 34, No. 4, pp. 418-420 (2007).

\* cited by examiner

FLOWABLE BULK GRANULAR POLYSACCHARIDE

This application claims the benefit of U.S. Provisional Application Nos. 62/571,995 (filed Oct. 13, 2017) and 62/725,532 (filed Aug. 31, 2018), which are incorporated herein by reference in their entirety.

FIELD

The present disclosure is in the field of polysaccharide materials. For example, the disclosure pertains to compositions comprising insoluble alpha-glucan particles having advantageous flow properties.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., Microbiology 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

Typically, bulk granular materials with high moisture contents have poor material handling characteristics such as low flowability, which can negatively impact downstream operations (e.g., storage and transport) with such materials. Expensive and complicated equipment are generally necessary to handle high moisture bulk materials. Addressing this problem with respect to polysaccharide-based materials, disclosed herein are high moisture insoluble alpha-glucan compositions with advantageous flow properties.

SUMMARY

In one embodiment, the present disclosure concerns a composition comprising particles with an average size of about 0.1-10 mm, wherein the particles comprise at least (i) about 50%-90% by weight water or an aqueous solution, and (ii) about 10%-50% by weight insoluble alpha-glucan or an insoluble cationic ether thereof, wherein the insoluble alpha-glucan comprises alpha-1,3-glycosidic linkages and has a weight-average degree of polymerization (DPw) of at least 100.

In another embodiment, the present disclosure concerns a method of preparing a composition as disclosed herein, the method comprising: (a) providing a first composition comprising at least (i) about 50%-90% by weight water or an aqueous solution, and (ii) about 10%-50% by weight insoluble alpha-glucan or an insoluble cationic ether thereof, and (b) providing particles of the first composition with an average size of about 0.1-10 mm.

In another embodiment, the present disclosure concerns a system for storing and/or moving a composition as disclosed herein, wherein the system comprises a container with at least one openable/closable discharge outlet located in the bottom portion of the container, wherein at least a portion of the container is tapered towards the discharge outlet, and wherein the composition is in the container and continuously flows out of the container when the discharge outlet is open.

In another embodiment, the present disclosure concerns a system for transporting a composition as disclosed herein, wherein the system comprises a conduit and gas to transport the composition through the conduit, optionally wherein the operating pressure of the system is about 5-105 psia, and optionally wherein the gas is air or an inert gas.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include alpha-1,3-glucan.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, wherein at least about 30% of the glycosidic linkages are alpha-1,3. Alpha-1,3-glucan in certain embodiments comprises at least about 90% or 95% alpha-1,3 glycosidic linkages. Most or all of the other linkages in alpha-1,3-glucan herein typically are alpha-1,6, though some linkages may also be alpha-1,2 and/or alpha-1,4.

The terms "glycosidic linkage", "glycosidic bond", "linkage" and the like are used interchangeably herein and refer to the covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. The term "alpha-1,6-glycosidic linkage" as used herein refers to the covalent bond that joins alpha-D-glucose molecules to each other through carbons 1 and 6 on adjacent alpha-D-glucose rings. The glycosidic linkages of a glucan polymer herein can also be referred to as "glucosidic linkages". Herein, "alpha-D-glucose" is referred to as "glucose".

The glycosidic linkage profile of an alpha-glucan herein can be determined using any method known in the art. For example, a linkage profile can be determined using methods using nuclear magnetic resonance (NMR) spectroscopy (e.g., $^{13}C$ NMR or $^{1}H$ NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as DPw (weight average degree of polymerization) or DPn (number average degree of polymerization). The molecular weight of smaller alpha-glucan polymers such as oligosaccharides typically can be provided as "DP" (degree of polymerization), which simply refers to the number of glucoses comprised within the alpha-glucan. Various means are known in the art for calculating these various molecular weight measurements such as with high-pressure liquid chromatography (HPLC), size exclusion chromatography (SEC), or gel permeation chromatography (GPC).

The terms "particle", "particulate", "granule", "grain", "fleck" and other like terms are interchangeably used herein. A particle herein has an average size (or average nominal size) of about 0.1-10 mm (millimeter). The terms "particulated", "granulated", and other like terms, can be used to characterize particles of insoluble glucan (or cationic ether thereof) herein. Particle size in some aspects can refer to particle diameter and/or the length of the longest particle dimension. The average size can be based on the average of diameters and/or longest particle dimensions of at least 50, 100, 500, 1000, 2500, 5000, or 10000 or more particles, for example.

The term "powder-like" and similar terms can optionally be used herein to characterize granulated insoluble glucan (or cationic ether thereof) as resembling a powder in texture and/or appearance. A "powder" is generally defined as any solid substance reduced to a state of fine, loose particles, with a water content of less than 20 wt % (typically lower such as less than 15, 10, 5, 3, 1, 0.5, or 0.1 wt %). The term powder-like differentiates from powder as defined above, since the disclosed composition has at least about 50 wt % water or aqueous solution.

A "particle-forming device" and other like terms herein refer to any device that can be used to prepare particles of insoluble glucan (or cationic ether thereof) from a larger form/preparation of the insoluble glucan (or cationic ether thereof) such as a filter cake.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009).

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components.

A "cake" of insoluble alpha-glucan (or cationic ether thereof) herein refers to a preparation in condensed, compacted, packed, squeezed, and/or compressed form that comprises at least (i) about 50%-90% by weight water or an aqueous solution, and (ii) about 10%-50% by weight insoluble alpha-glucan. A cake in some aspects can be referred to as a "filter cake" or a "wet cake".

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "sequence identity", "identity" and the like as used herein with respect to a polypeptide amino acid sequence are as defined and determined in U.S. Pat. Appl. Publ. No. 2017/0002336, which is incorporated herein by reference.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 80 wt % water.

A glucan, or cationic ether derivative thereof, that is "insoluble", "aqueous-insoluble", "water-insoluble" (and like terms) (e.g., insoluble alpha-1,3-glucan) does not dissolve (or does not appreciably dissolve) in water or other aqueous conditions, optionally where the aqueous conditions are further characterized to have a pH of 4-9 (e.g. pH 6-8) and/or temperature of about 1 to 85° C. (e.g., 20-25° C.). In contrast, glucans such as certain oligosaccharides herein that are "soluble", "aqueous-soluble", "water-soluble" and the like (e.g., alpha-1,3-glucan with a DP less than 8) appreciably dissolve under these conditions.

Terms used herein regarding alpha-glucan ether, particularly a "cationic alpha-glucan ether" such as cationic alpha-1,3-glucan ether, are defined as in U.S. Pat. Appl. Publ. No. 2016/0311935, which is incorporated herein by reference. The term "degree of substitution" (DoS) as used herein refers to the average number of hydroxyl groups substituted (with a positively charged organic group via ether linkage) in each monomeric unit (glucose) of an alpha-1,3-glucan ether. Insoluble cationic alpha-1,3-glucan ethers herein can have a DoS of up to about 0.3 (e.g., 0.001 to 0.3), since a higher DoS (>0.3) in some aspects can be associated with soluble cationic alpha-1,3-glucan ethers.

A "positively charged organic group" as used herein refers to a chain of one or more carbons ("carbon chain") that has one or more hydrogens substituted with another atom or functional group (e.g., a "substituted alkyl group"), where one or more of the substitutions is with a positively charged group. Where a positively charged organic group has a substitution in addition to a substitution with a positively charged group, such additional substitution may be with one or more hydroxyl groups, oxygen atoms (thereby forming an aldehyde or ketone group), alkyl groups, and/or additional positively charged groups. A positively charged organic group has a net positive charge since it comprises one or more positively charged groups. The terms "positively charged group", "positively charged ionic group", "cationic group" and the like are used interchangeably herein. A positively charged group comprises a cation (a positively charged ion). Examples of positively charged groups include substituted ammonium groups, carbocation groups and acyl cation groups.

The terms "outlet", "discharge outlet", "exit" and other like terms herein refer to an openable/closable opening that, when open, can allow a material to exit a container (discharge from a container). One or more discharge outlets typically can be located at the bottom of, or elsewhere in the bottom portion of, a container. In some aspects, the "diameter" of a discharge outlet refers to the diameter (if outlet is circular) or longest diameter (if outlet is elliptical) of the smallest cross-sectional area of the discharge outlet. A discharge outlet herein typically projects (aims) underneath a container.

The term "tapered" and like terms herein refer to a narrowing (e.g., gradual and/or uniform narrowing) of a portion of a container toward a discharge outlet. Such narrowing typically extends down to the smallest cross-sectional area of the discharge outlet. "Degrees from vertical" as used herein characterizes the relative steepness of tapering. The steepness of tapering increases as its degrees from vertical decreases; e.g., a tapering of 60 degrees from vertical is less steep (i.e., has a lower grade) than a tapering of 30 degrees from vertical. It should be understood that 0 degrees from vertical represents no tapering. Optionally, "degrees from horizontal" can be used to describe tapering, and is calculated simply by subtracting the degrees from vertical from 90 degrees.

A "container" having one or more discharge outlets herein typically is suitable for holding/storing and/or transporting at least about 100 kg (kilograms) of insoluble alpha glucan particles of the present disclosure.

As used herein, "psia" (pounds per square inch absolute) refers to a unit of pressure relative to a vacuum rather than atmospheric pressure. Atmospheric pressure is 14.7 psia, for example. A pressure of 5 psia, for example, characterizes a partial vacuum.

The term "isolated" means a substance (or process) in a form or environment that does not occur in nature. A non-limiting example of an isolated substance includes any non-naturally occurring substance such as a granulated insoluble glucan herein (as well as the enzymatic reactions and other processes used to prepare it). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

Expensive and complicated equipment are generally necessary to handle high moisture bulk materials. Addressing this problem with respect to polysaccharide-based materials, disclosed herein are high moisture insoluble alpha-glucan compositions with advantageous flow properties.

Certain embodiments of the present disclosure concern a composition comprising, or consisting of, particles with an average size of about 0.1-10 mm. These particles comprise, or consist of, at least, (i) about 50%-90% by weight water or an aqueous solution, and (ii) about 10%-50% by weight insoluble alpha-glucan or an insoluble cationic ether thereof, wherein the insoluble alpha-glucan comprises alpha-1,3-glycosidic linkages and has a weight-average degree of polymerization (DPw) of at least 100. Such high moisture, insoluble alpha-glucan compositions have advantageous flow properties, which enable more economic storage and transport processes.

A composition herein comprises particles with an average size of about 0.1-10 mm. In some aspects, the average size of the particles is about 0.1-7, 0.1-6, 0.1-5, 0.1-4, 0.1-3, 0.1-2, 0.5-7, 0.5-6, 0.5-5, 0.5-4, 0.5-3, 0.5-2, 1-7, 1-6, 1-5, 1-4, 1-3, 1-2, 1-10, 2-10, 2-8, 2-6, 2-4, 4-10, 4-8, 4-6, 6-10, 6-8, 8-10, 5-10, 5-7, 6-7, 1, 2, 3, 4, 5, 6, 7, 8, 9, or 10 mm. Isolation of particles of any of these size ranges can be done using appropriately sized meshes/sieves, for example. These tools can also be used to determine/confirm particle size. The particles of the disclosed composition are equal or less than about 7, 6, 5, 4, 3, or 2 mm in some aspects. Particle size in some aspects can optionally be characterized in terms of the particle size produced by forcibly transiting insoluble alpha-glucan through a particle-forming device comprising a screen/sieve (e.g., a grater) with 1-, 2-, 3-, 4-, 5-, 6-, 7-, 8-, 9-, and/or 10-mm passages (or through passages as described below for particle-forming device). Particles produced in this manner typically are of a size equal to or less than the size(s) of the passages.

Particles in a composition herein comprise about 50%-90% by weight water or an aqueous solution. In some aspects, particles can comprise about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 50-90, 50-80, 50-70, 50-60, 55-80, 60-90, 60-80, 60-70, 55-65, 55-80, or 70-80 wt % water or an aqueous solution. Though such particles have a high moisture content, a composition comprising them is not in the form of a slurry, colloidal dispersion, or other liquid/fluid form. Rather, a composition in some aspects can be characterized as being powder-like (resembling a powder) in appearance and/or texture, though the particles of the composition have a liquid water content much higher than that of a typical powder (see above definition).

Water or an aqueous solution is comprised within particles herein. An aqueous solution in some aspects has no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. An aqueous solution in some aspects can have one or more salts/buffers (e.g., $Na^+$, $Cl^-$, NaCl, phosphate, tris, citrate) (e.g., ≤0.1, 0.5, or 1.0 wt %) and/or a pH as listed below for glucosyltransferase reaction conditions (e.g., pH 6.0-8.0). In some aspects, the solvent of an aqueous solution herein can comprise about, or at least about, 80, 85, 90, 95, 96, 97, 98, 99, 99.5, or 100 wt % water; the rest of the solvent can be a polar organic solvent, for example.

Particles in a composition herein comprise about 10%-50% by weight insoluble alpha-glucan and/or one or more insoluble cationic ethers thereof. In some aspects, particles can comprise about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 10-50, 10-40, 10-30, 10-20, 20-50, 20-45, 20-40, 20-30, 30-50, 30-40, 40-50, 30-45, 35-45, 37.5-42.5, 35-40, or 40-45 wt % insoluble alpha-glucan and/or one or more insoluble cationic ethers thereof. Particles in some aspects comprise insoluble alpha-glucan and no cationic ether thereof (and vice versa). Insoluble alpha-glucan is not derivatized (not chemically modified such as etherified) in some aspects.

Particles in a composition herein can comprise, or consist of, water and insoluble alpha-glucan (and/or insoluble cationic ether thereof), and optionally any of the other components as disclosed above (e.g., dissolved sugars, salt, buffer, and/or polar organic solvent). Particles herein typically do not comprise, or have less than about 0.5, 0.1, or 0.05 wt % of (or do not have a detectable amount of), any other substance such as a filler (e.g., wood, pulp, or any other solid substance) or plasticizer (e.g., glycerol).

A composition comprising particles herein can be at a temperature of about 4-30, 10-30, 15-30, 20-30, 25-30, 15-25, or 20-25° C., for example. In some embodiments, a composition comprising particles (e.g., particles as present in a bulk amount, such as in a shipping container) can weigh at least about 100, 200, 250, 300, 400, 500, 600, 700, 800, 900, 1000, 1100, or 1200 kg, or at least about 1, 1.5, 2, 2.5, 5, 10, 20, 25, 50, 75, or 100 tons (US or metric), and/or have a density of about 35, 36, 37, 38, 39, 40, 41, 42, 35-42, 35-40, 37-42, or 37-40 pounds/cubic foot following compression of about 50-550 pounds/square foot). Significantly, particles in such high weight and/or density embodiments exhibit continuous flowability from commercial-size/bulk containers (as described below). The density of loose bulk material (i.e., a composition that has not been subject to any compression procedure) herein can be about 31-38, 31-37, 32-38 or 32-37 pounds/cubic foot, for example.

Particles in some aspects can comprise about 10%-50% by weight insoluble alpha-glucan that comprises alpha-1,3-glycosidic linkages and has a weight-average degree of polymerization (DPw) of at least 100. In some aspects, at least about 50%, 60%, 70%, 80%, 85%, 90%, 91%, 92%, 93%, 94%, 95%, 96%, 97%, 98%, 99%, 99.5%, or 100% (or any integer between 50% and 100%) of the constituent glycosidic linkages of insoluble alpha-glucan are alpha-1,3 linkages. In some aspects, accordingly, insoluble alpha-glucan has less than about 50%, 40%, 30%, 20%, 15%, 10%, 9%, 8%, 7%, 6%, 5%, 4%, 3%, 2%, 1%, 0.5%, or 0% (or any integer value between 0% and 50%) glycosidic linkages that are not alpha-1,3. Typically, the linkages that are not alpha-1,3 are mostly or entirely alpha-1,6. It should be understood that the higher the percentage of alpha-1,3 linkages present in alpha-glucan, the greater the probability that the alpha-glucan is linear, since there are lower occurrences of certain linkages forming branch points in the polymer. Thus, insoluble alpha-glucan with 100% alpha-1,3 linkages is believed to be completely linear. In certain embodiments, insoluble alpha-glucan has no branch points or less than about 5%, 4%, 3%, 2%, or 1% branch points as a percent of the glycosidic linkages in the polymer. Examples of branch points include alpha-1,6, -1,2 and -1,4 branch points stemming from an alpha-1,3-linked backbone.

Insoluble alpha-glucan herein can have a molecular weight in DPw or DPn of at least about 100 in some aspects. DPw or DPn in some embodiments can be about, or at least about, 100, 150, 200, 250, 300, 350, 400, 450, 500, 550, 600, 650, 700, 750, 800, 850, 900, 950, 1000, 1100, or 1200 (or any integer between 100 and 1200). The DPw or DPn of an alpha-glucan can optionally be expressed as a range between any two of these values (e.g., 100-1200, 400-1200, 700-1200, 100-1000, 400-1000, 700-1000).

Alpha-glucan herein is insoluble in non-caustic aqueous systems, such as those conditions of a glucosyltransferase reaction herein (e.g., pH 4-8, see below). In general, the solubility of a glucan polymer in aqueous settings herein is related to its linkage profile, molecular weight, and/or degree of branching. For example, alpha-1,3-glucan with ≥95%, 1,3 linkages is generally insoluble at a DPw of 8 and above in aqueous conditions at 20° C. In general, as molecular weight increases, the percentage of alpha-1,3 linkages required for alpha-1,3-glucan insolubility decreases.

In some embodiments, an insoluble alpha-glucan can comprise at least about 30% alpha-1,3 linkages and a percentage of alpha-1,6 linkages that brings the total of both the alpha-1,3 and -1,6 linkages in the alpha-glucan to 100%. For example, the percentage of alpha-1,3 and -1,6 linkages can be about 30-40% and 60-70%, respectively. In some aspects, an insoluble alpha-glucan comprising at least about 30% alpha-1,3 linkages is linear. Glucosyltransferases for producing insoluble alpha-glucan comprising at least about 30% alpha-1,3 linkages are disclosed in U.S. Pat. Appl. Publ. No. 2015/0232819, which is incorporated herein by reference.

Insoluble alpha-glucan in some embodiments can be in the form of a copolymer (e.g., graft copolymer) having (i) a backbone comprising dextran (e.g., with at least about 95%, 96%, 97%, 98%, 99%, or 100% alpha-1,6 linkages) with a molecular weight of at least about 100000 Daltons, and (ii) alpha-1,3-glucan side chains comprising at least about 95%, 96%, 97%, 98%, 99%, or 100% alpha-1,3-glucosidic linkages. Such copolymers can be as disclosed in Int. Pat. Appl. Publ. No. WO2017/079595, which is incorporated herein by reference.

Any of the foregoing linkage profiles and/or molecular weight profiles, for example, can be combined herein to appropriately characterize insoluble alpha-glucan herein. In some aspects, the linkage and/or molecular weight profile of such alpha-glucan can be as disclosed in any of the following publications, all of which are incorporated herein by reference: U.S. Pat. Nos. 7,000,000 and 8,871,474, U.S. Patent Appl. Publ. No. 2015/0232819, Int. Pat. Appl. Publ. No. WO2017/079595. Insoluble alpha-glucan of the foregoing embodiments can be a product of any of the glucan synthesis reaction processes disclosed below, for example.

Insoluble alpha-glucan herein does not comprise alternan (alternating 1,3 and 1,6 linkages), which is aqueous-soluble. Insoluble alpha-glucan herein is typically enzymatically derived in an inert vessel (typically under cell-free conditions), and is not derived from a cell wall (e.g., fungal cell wall).

Insoluble alpha-glucan in some aspects can be enzymatically produced in a reaction composition comprising at least water, sucrose and a glucosyltransferase enzyme that synthesizes insoluble alpha-glucan. Such an enzymatic reaction can employ a glucosyltransferase enzyme that produces any insoluble alpha-glucan molecule as disclosed above (e.g., 90% or 95% alpha-1,3-linkages).

A glucosyltransferase enzyme in certain embodiments for producing insoluble alpha-glucan can comprise an amino acid sequence as disclosed in any of U.S. Patent Appl. Publ. Nos. 2014/0087431, 2017/0166938, 2017/0002335, and 2018/0072998 (U.S. application Ser. No. 15/702,893) (all of which are incorporated herein by reference), for example. Examples of such sequences include those that are 100% identical to, or at least 90%, 91%, 92%, 93%, 94%, 95%, 96%, 97%, 98%, 98.5%, 99%, or 99.5% identical to, SEQ ID NO:2, 4, 6, 8, 10, 12, 14, 16, 18, 20, 26, 28, 30, 34, or 59 as disclosed in U.S. Patent Appl. Publ. No. 2014/0087431, and have glucosyltransferase activity. A glucosyltransferase enzyme with SEQ ID NO:2, 4, 8, 10, 14, 20, 26, 28, 30, or 34 as disclosed in U.S. Patent Appl. Publ. No. 2014/0087431 can synthesize insoluble alpha-1,3-glucan comprising at least about 90% alpha-1,3-glycosidic linkages in some aspects.

The amino acid sequence of a glucosyltransferase enzyme in certain aspects has been modified such that the enzyme produces more products (insoluble alpha-glucan and fructose), and less by-products (e.g., glucose, oligosaccharides such as leucrose), from a given amount of sucrose substrate. For example, one, two, three, four, or more amino acid residues of the catalytic domain of a glucosyltransferase herein can be modified/substituted to obtain an enzyme that produces more products (insoluble alpha-glucan and fructose).

A glucosyltransferase enzyme herein can be derived from any microbial source, such as bacteria. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about 20-400 g/L, 75-175 g/L, or 50-150 g/L, for example. In some aspects, the initial sucrose concentration is at least about 50, 75, 100, 150 or 200 g/L, or is about 50-600 g/L, 100-500 g/L, 50-100 g/L, 100-200 g/L, 150-450 g/L, 200-450 g/L, or 250-600 g/L. "Initial concentration of sucrose" refers to the sucrose concentration in a reaction composition just after all the reaction components have been added/combined (e.g., at least water, sucrose, glucosyltransferase enzyme).

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 10 mM, 20 mM, or 50 mM, for example.

A glucosyltransferase reaction can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein) can be about, or at least about, 1, 10, 50, 100, 500, 1000, 2500, 5000, 10000, 12500, 15000, or 20000 liters. An inert vessel can optionally be equipped with a stirring device. Any of the foregoing features, for example, can be used to characterize an isolated reaction herein.

A reaction composition herein can contain one, two, or more glucosyltransferase enzymes, for example. In some embodiments, only one or two glucosyltransferase enzymes is/are comprised in a reaction composition. A glucosyltransferase reaction herein can be, and typically is, cell-free (e.g., no whole cells present).

Completion of a reaction in certain embodiments can be determined visually (e.g., no more accumulation of insoluble alpha-glucan), and/or by measuring the amount of sucrose left in the solution (residual sucrose), where a percent sucrose consumption of at least about 90%, 95%, or 99% can indicate reaction completion. In some aspects, a reaction can be considered complete when its sucrose content is at or below about 2-5 g/L. A reaction of the disclosed process can be conducted for about 1 hour to about 2, 4, 6, 8, 10, 12, 14, 16, 18, 20, 22, 24, 36, 48, 60, 72, 96, 120, 144, or 168 hours, for example. A reaction can optionally be terminated and/or otherwise treated to stop glucosyltransferase activity (e.g., by heating it to at least about 65° C. for at least about 30-60 minutes).

Examples of other conditions and/or components suitable for synthesizing insoluble alpha-glucan herein are disclosed in U.S. Patent Appl. Publ. Nos. 2014/0087431, 2017/0166938 and 2017/0002335, which are incorporated herein by reference.

Insoluble alpha-glucan produced in a glucosyltransferase reaction herein is typically isolated as a cake comprising at least (i) about 50%-90% by weight water or an aqueous solution, and (ii) about 10%-50% by weight insoluble alpha-glucan. Such cake can optionally be characterized as a filter cake or wet cake, and can be used to prepare particles of the present disclosure (see below). Isolating insoluble alpha-glucan for cake preparation can include at least conducting a step of centrifugation (cake is pelleted glucan) and/or filtration (cake is filtered glucan). For example, wet cake herein can be obtained using a funnel, filter (e.g., a surface filter such as a rotary vacuum-drum filter, cross-flow filter, screen filter, belt filter, screw press, or filter press with or with membrane squeeze capability; or a depth filter such as a sand filter), and/or centrifuge; filtration can be by gravity, vacuum, or press filtration, for instance. Isolation can optionally further comprise washing the centrifuged and/or filtered alpha-glucan one, two, or more times with water or other aqueous liquid. A wash volume can optionally be at least about 10-100% of the volume of the glucosyltransferase reaction used to produce the insoluble alpha-glucan, for example. Washing can be done by various modes, as desired, such as by displacement or re-slurry washing. In some aspects, the aqueous portion of the resulting cake has no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. Insoluble alpha-glucan herein typically is not dried after its enzymatic synthesis and prior to processing it to powder form; thus, alpha-glucan herein can optionally be characterized as having never been dried.

Particles in some aspects can comprise about 10%-50% by weight of an insoluble cationic ether of an insoluble alpha-glucan. Such an ether can be, for example, a cationic ether derivative of any insoluble alpha-glucan as disclosed herein. Simply as an example, an alpha-1,3-glucan for ether-derivatization can (i) have about, or at least about, 90%, 95%, 96%, 97%, 98%, 99%, or 100% alpha-1,3 linkages, and/or (ii) a DPw of about, or at least about, 100, 250, 500, 600, 700, 800, 900, 1000, 1100, 1200, 500-1200, 500-1100, 500-1000, 500-900, 500-800, 800-1200, 800-1100, 800-1000, or 800-900. While a single type of insoluble cationic ether can typically be used, two or more types of insoluble cationic ether can optionally be used. In some aspects, an insoluble cationic ether comprises one type of positively charged organic group, while in other aspects an insoluble cationic ether comprises two or more types of positively charged organic group.

The DoS (with a positively charged ether group) of an insoluble cationic alpha-glucan ether herein can be up to about (or from 0.001 to about) 0.3, 0.29, 0.28, 0.27, 0.26, 0.25, 0.24, 0.23, 0.22, 0.21, 0.2, 0.15, or 0.1, or about 0.01-0.3, 0.01-0.25, 0.01-0.2, 0.01-0.15, 0.01-0.1, 0.05-0.3, 0.05-0.25, 0.05-0.2, 0.05-0.15, or 0.05-0.1, for example. A positively charged group can be, for example, any of those disclosed in U.S. Pat. Appl. Publ. No. 2016/0311935, which is incorporated herein by reference. A positively charged group can comprise a substituted ammonium group, for example. Examples of substituted ammonium groups are primary, secondary, tertiary and quaternary ammonium groups. An ammonium group can be substituted with one, two, or three alkyl groups (e.g., methyl, ethyl, propyl, butyl, pentyl, hexyl, heptyl, octyl, nonyl, decyl), for example. One of the groups of a substituted ammonium group comprises one carbon, or a chain of carbons, in ether linkage to a graft copolymer; such a carbon or carbon chain can be —CH$_2$—, —CH$_2$CH—, —CH$_2$CH$_2$CH$_2$—, —CH$_2$CH$_2$CH$_2$CH$_2$—, or —CH$_2$CH$_2$CH$_2$CH$_2$CH$_2$—, for example. A carbon or carbon chain in this context can optionally have at least one substitution with an oxygen atom (e.g., alcohol group) and/or alkyl group (e.g., methyl, ethyl, propyl, butyl). One or more positively charged organic groups in some aspects can be trimethylammonium hydroxypropyl groups (structure I, when each of R$_2$, R$_3$ and R$_4$ is a methyl group).

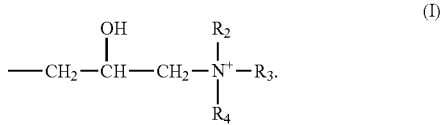

(I)

Certain embodiments of the present disclosure concern a method of preparing a composition comprising particles as described herein. Such a method can comprise: (a) providing a first composition comprising at least (i) about 50%-90% by weight water or an aqueous solution, and (ii) about 10%-50% by weight insoluble alpha-glucan or an insoluble cationic ether thereof, and (b) providing particles of the first composition with an average size of about 0.1-10 mm (e.g., by contacting the first composition with a suitable particle-forming device). Such a method can optionally be characterized herein as an insoluble alpha-glucan (or insoluble cationic ether thereof) particle-forming method.

A first composition for use in an insoluble alpha-glucan particle-forming method herein can be a cake of insoluble alpha-glucan as disclosed above (e.g., filter cake or wet cake), for example. Such a cake can comprise about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 50-90, 50-80, 50-70, 50-60, 60-90, 60-80, 60-70, 55-65, 55-80, or 70-80 wt % water or an aqueous solution. An aqueous solution in a cake in some embodiments can have no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. An aqueous solution in a cake in some aspects can have one or more salts/buffers (e.g., Na$^+$, Cl$^-$, NaCl, phosphate, tris, citrate) (e.g., 0.1, 0.5, or 1.0 wt %) and/or a pH as listed above for glucosyltransferase reaction conditions (e.g., pH 6.0-8.0). In some aspects, the solvent of an aqueous solution herein can comprise about, or at least about, 80, 85, 90, 95, 96, 97, 98, 99, 99.5, or 100 wt % water; the rest of the solvent can be a polar organic solvent, for example. A cake of insoluble alpha-glucan or insoluble cationic ether thereof can comprise about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 10-50, 10-40, 10-30, 10-20, 20-50, 20-40, 20-30, 30-50, 30-40, 40-50, 30-45, 35-45, 37.5-42.5, 35-40, or 40-45 wt % insoluble alpha-glucan or insoluble cationic ether thereof, for example. Such a cake can comprise, or consist of, water and insoluble alpha-glucan (and/or insoluble cationic ether thereof), and optionally any of the other components as disclosed above (e.g., dissolved sugars, salt, buffer, and/or polar organic solvent). A cake herein typically does not comprise, or has less than about 0.5, 0.1, or 0.05 wt % of (or do not have a detectable amount of), any other substance such as a filler (e.g., wood, pulp, or any other solid substance) or plasticizer (e.g., glycerol).

An insoluble alpha-glucan particle-forming method comprises step (b) of providing particles of the first composition with an average size of about 0.1-10 mm. Water typically is not added during this step (i.e., water is not added that is in addition to the water already present in the first composition). Providing particles in some aspects can comprise contacting a first composition (e.g., an insoluble alpha-glucan cake) with a suitable particle-forming device, such that particles of the first composition with an average size of about 0.1-10 mm are produced. This particle-forming step can optionally be characterized as granulation or particulation. A particle-forming step in some aspects can be performed such that particles of a certain average size range are directly prepared; this can be done using an suitable particle-forming device with appropriate size dimensions, for example. Additionally or alternatively, particles of a certain average size range can be prepared by applying a suitable size selection tool (e.g., screen/sieve) to a population of particles. Average particle sizes produced in step (b) can be any of those sizes/ranges listed above, for example. Particle formation can optionally be performed using an insoluble alpha-glucan cake that has first been chopped, crumbled, and/or otherwise broken into pieces smaller than the cake.

A particle-forming device in some aspects can be a shredder, shaver, grater, tumbler, screen, sieve, grinder, or mill, for example. One or more particle-forming devices can be employed, as desired. A particle-forming device in some aspects comprises a plurality of 0.1-mm to 10-mm passages through which the first composition (e.g., an insoluble alpha-glucan cake) is forcibly transited. Examples of such a device include a screen or sieve (such as that of a grater). The dimensions of the passages (e.g., mesh size) of a screen/sieve herein can be any of those dimensions listed above for average particle sizes, for example. For example, a screen/sieve can have approximately 1-, 2-, 3-, 4-, 5-, 6-, 7-, 8-, 9-, and/or 10-mm passages. Also for example, a screen/sieve can have mesh with the following approximate passage sizes (corresponding to certain commercially available screens/sieves): 9.5, 8.0, 6.7, 6.4, 6.3, 5.7, 5.7, 4.8, 4.0, 3.4, 2.8, 2.4, 2.0, 1.7, 1.4, 1.2, 1.0, 0.8, 0.7, 0.6, 0.5, 0.4, 0.35, 0.3, 0.25, 0.2, 0.15, or 0.1 mm. Also for example, a screen/sieve can have mesh with the following U.S. sieve/mesh designations: ⅜ in., 5/16 in., 0.265 in., ¼ in., No. 3½, No. 4, No. 5, No. 6, No. 7, No. 8, No. 10, No. 12, No. 14, No. 16, No. 18, No. 20, No. 25, No. 30, No. 35, No. 40, No. 45, No. 50, No. 60, No. 70, No. 80, No. 100, or No. 120. While the passages of a screen/sieve herein typically are square or of another four-cornered shape, the passages can be other shapes (e.g., circular/elliptical) in some aspects.

Certain embodiments of the present disclosure concern a system for storing and/or moving a composition comprising particles as described herein. Such a system comprises a container with at least one openable/closable discharge outlet located in the bottom portion of the container, wherein at least a portion of the container is tapered towards the discharge outlet, and wherein the composition is in the container and continuously flows out of the container when the discharge outlet is open.

A container herein typically is suitable (has a capacity) for holding/storing at least about 100, 200, 250, 300, 400, 500, 600, 700, 800, 900, 1000, 1100, or 1200 kg, or at least about 1, 2, 5, 10, 20, 25, 50, 75, or 100 tons (US or metric), of insoluble alpha-glucan particles of the present disclosure. A container herein can optionally be characterized as a commercial (commercial-size) container, bulk container, storage container, shipping or freight container, and other like terms, optionally depending on how the container is used. A container can be a bin (e.g., rigid-walled bin), hopper, silo, flexible intermediate bulk container (FIBC) (a.k.a. bulk bag; e.g., Super Sacks™), or other container suitable for storing and/or transporting a large amount (e.g., at least 100 kg) of the presently disclosed particles, for example. In some aspects, the inside wall of a container (i.e., the surface that is in contact with particles) can be made of metal (e.g., stainless steel) or plastic (wall of the container is plastic, or container has a plastic liner). Some containers (e.g., hoppers or silos) can contain internal components such as an outlet cone (conical insert with a closed apex oriented upwards) and/or internal funnel (a.k.a. cone-in-cone) with an open outlet supported above the outlet and concentric with the outlet.

A system as presently disclosed can optionally encompass a facility for producing and/or storing insoluble alpha-glucan (or insoluble ether thereof) particles; a container therein can optionally be characterized as a stationary container. Such a system can be considered a factory and/or storage facility in some instances. In some embodiments, a system can encompass an element for transporting the disclosed particles, such as a truck (e.g., tractor trailer) or train/rail car; a container therein can optionally be characterized as a shipping or freight container.

A container herein has at least one openable/closable discharge outlet located in the bottom portion of the container. There can be 1, 2, 3, 4, or more outlets, for example. In typical embodiments, a discharge outlet is located at the bottom side of the container, and is centrally located if the container has a single outlet (in a container with two or more outlets, they are typically equally spaced along the central axis of the longest bottom dimension). However, an outlet can project laterally from the bottom portion of a container in some aspects. An outlet herein typically is circular, elliptical, square (or another four-cornered shape), or triangular.

At least a portion(s) of the container is tapered towards its one or more discharge outlets. The horizontal cross-sections (imaginary slices) of the tapering are typically, but not necessarily, of the same shape as the outlet(s). Containers with one discharge outlet can optionally be tapered along its entire vertical length, or most of (e.g., 80 or 90%) its vertical length, or the tapering can represent a smaller portion (e.g., 70, 60, 50, 40, 30, 20, or 10%) of the container's vertical length. The outlet shape in single outlet embodiments herein is typically the same as the shape of the horizontal cross-sections (imaginary slices) of the container. In some aspects, the tapering towards an outlet is about, or at least about, 60, 55, 50, 45, 40, 35, 30, 25, 20, 15, 25-50, 30-50, 25-45, or 30-45 degrees from vertical. Tapering in some aspects can (i) be of a single slope (degrees from vertical constant from beginning of taper to its end at the outlet), (ii) have two or more slopes (a greater degrees from vertical tapering meets a lower degrees from vertical at each slope transition approaching the outlet), or (iii) have a gradually increasing slope (slope curves from less to more steep approaching the outlet).

The smallest cross-sectional area of a discharge outlet in some aspects has a span of about, or at least about, 4, 5, 6, 7, 8, 9, 10, 11, 12, 14, 16, 18, 24, 30, 36, 42, 48, 4-48, 8-48, 10-48, 4-36, 8-36, 10-36, 4-24, 8-24, 10-24, 4-18, 8-18, 10-18, 4-12, 8-12, 10-12, 4-10, 8-10, or 4-8 inches. Such a span can optionally be referred to as diameter or longest diameter with an outlet that is circular or elliptical, respectively. The span of a triangular, square, or other non-round outlet typically is the longest dimension (or internal dimension, whichever is longer) of the outlet cross-sectional area.

A discharge outlet in some aspects can be operably linked to a conduit such as a pipe, tube, hose, chute, cylinder, or duct. Such an operably linked conduit can be physically part of the container (e.g., pipe that is welded or otherwise continuous with the container body), or a separate device/mechanism that is otherwise in communication with the outlet. An operably linked conduit can help direct the flow of particles out of the container to a different vessel, for example. The span of the smallest cross-sectional area of an operably linked conduit typically is not smaller than the span of the smallest cross-sectional area of the outlet.

A discharge outlet herein should not be confused with any other opening of a container, such as a top or top-side opening used to put material into the container, or an opening allowing entry/positioning of an auxiliary feature such as a wire (e.g., electrical power cord), mechanical device, or detection/monitoring device.

A container herein can have, or can lack, a device that promotes the flow ("flow promotion device") of the disclosed particles out of the container when the discharge outlet is open. A container in some aspects (i) does not comprise a flow promotion device, or (ii) comprises a flow promotion device, but which is not required to be active in order for the particles to flow out of the container when the discharge outlet is open. A flow promotion device can comprise a vibrator, gyrator, mechanical agitator (e.g., screw feeder), pneumatic device (e.g., air cannon, air pillow), or any other device or action, for example, that motivates flow of particulates through the discharge outlet(s) of a container when activated. A flow-promotion device can optionally be characterized as a "live-bottom" device in some aspects. A flow promotion device can be situated inside a container (e.g., in direct contact with the disclosed particles), or outside (but in communication with) the container. In some aspects, a flow promotion device can be activated/actuated for less than about 1, 2, 3, 4 or 5 seconds in order to initiate particle flow from the container, after which time the flow is continuous (and the flow promotion device remains off). Continuous flow of the disclosed particles refers to undisrupted flow (without needing continuous activation of a flow promotion device) that completely empties the container, or that only leaves a volume of particles in the container (upon flow ending) that is at most 5%, 4%, 3%, 2%, 1%, 0.5%, or 0.1% of the container's holding capacity volume, for example. The disclosed particles typically do not form bridges/arches, ratholes, and/or walls while the particles flow out of the container; in some aspects, such a particulate structure(s) might form temporarily, but readily falls apart as flow continues. A bridge/arch of bulk material is a bridge/arch structure occurring across an outlet's opening. A rathole is a self-supporting annular structure of bulk material leading to an outlet. Flow of particles herein does not require addition of any a component/ingredient that promotes flow of particulate material. Continuous flow herein is contemplated to be realized even following activities that compress the disclosed particles, such as particulate settling during road or rail transport.

Methods of storing and/or transporting the presently disclosed particles can comprise, at least, providing a container holding the particles, and opening a discharge outlet of the container to allow the particles to continuously flow out of the container. Any features described above or in the below Examples can optionally characterize such a method.

Certain embodiments of the present disclosure concern a system for transporting a composition comprising particles as described herein, which system comprises a conduit and gas (motive gas) to transport the composition through the conduit. Optionally, the operating pressure of the system is about 5-105 psia, and/or the motive gas is air or an inert gas. This system can be used, for example, to fill a container as disclosed herein, or to move the disclosed particles following storage and/or transport thereof in the container. This system can optionally be characterized as a pneumatic conveyance system. A conduit herein can be a pipe, tube, hose, chute, cylinder, duct or other like device/hardware.

The operating pressure of a pneumatic conveyance system herein can optionally be about 5-105 psia, excluding atmospheric pressure (14.7 psia). Such pressure can be applied within the conduit, thereby pushing or pulling the disclosed particles within the conduit (i.e., conveying the particles). In some aspects, operating pressure can be under atmospheric pressure (e.g., about 5-10 or 5-14 psia), thereby allowing for vacuum conveying of particles. In some aspects, operating pressure can be above atmospheric pressure (e.g., about 15-35, 15-30, 20-35, or 20-30 psia), allowing for positive pressure flow. Operating pressure can be provided to the system using a vacuum, blower, or compressed air device, for example. The gas used in a pneumatic conveyance system herein can be air or an inert gas, for example. An inert gas herein is one that does not react with (or otherwise cause a reaction involving) insoluble alpha-glucan herein. Examples of suitable inert gases include nitrogen, carbon dioxide, and argon.

Non-limiting examples of compositions and methods disclosed herein include:

1. A composition comprising particles with an average size of about 0.1-10 mm, wherein the particles comprise at least (i) about 50%-90% by weight water or an aqueous solution, and (ii) about 10%-50% by weight insoluble alpha-glucan or an insoluble cationic ether of the insoluble alpha-glucan, wherein the insoluble alpha-glucan comprises alpha-1,3-glycosidic linkages and has a weight-average degree of polymerization (DPw) of at least 100.

2. The composition of embodiment 1, wherein the insoluble alpha-glucan has at least 50% alpha-1,3-glycosidic linkages.

3. The composition of embodiment 1 or 2, wherein the particles comprise about 30%-45% by weight of the insoluble alpha-glucan or insoluble cationic ether thereof.

4. The composition of embodiment 1, 2, or 3, wherein the composition is powder-like.

5. The composition of embodiment 1, 2, 3, or 4, wherein the insoluble alpha-glucan is enzymatically produced in a reaction composition comprising at least water, sucrose and a glucosyltransferase enzyme that synthesizes insoluble alpha-glucan.

6. The composition of embodiment 1, 2, 3, 4, or 5, wherein the particles are produced by contacting a first composition with a particle-forming device, wherein the first composition comprises at least (i) about 50%-90% by weight water or an aqueous solution, and (ii) about 10%-50% by weight insoluble alpha-glucan.

7. The composition of embodiment 6, wherein the first composition is a cake of the insoluble alpha-glucan.

8. The composition of embodiment 1, 2, 3, 4, 5, 6, or 7, wherein the particles comprise said insoluble alpha-glucan.

9. A method of preparing a composition of any of embodiments 1-8, the method comprising: (a) providing a first composition comprising at least (i) about 50%-90% by weight water or an aqueous solution, and (ii) about 10%-50% by weight insoluble alpha-glucan or an insoluble cationic ether of the insoluble alpha-glucan, and (b) providing particles of the first composition with an average size of about 0.1-10 mm.

10. The method of embodiment 9, wherein the first composition is a cake of the insoluble alpha-glucan.

11. The method of embodiment 9 or 10, wherein step (b) comprises contacting the first composition with a particle-forming device, optionally wherein the particle-forming device comprises a plurality of 0.1-mm to 10-mm passages through which the first composition is forcibly transited, and optionally further wherein the particle-forming device comprises a screen.

12. A system for storing and/or moving a composition according to any of embodiments 1-8, wherein the system comprises a container with at least one openable/closable discharge outlet located in the bottom portion of the container, wherein at least a portion of the container is tapered towards the discharge outlet, and wherein the composition is in the container and continuously flows out of the container when the discharge outlet is open.

13. The system of embodiment 12, wherein the container is a hopper, bin, silo, or bulk bag.

14. The system of embodiment 12 or 13, wherein the smallest cross-sectional area of the discharge outlet has a span of at least about 4 inches.

15. The system of embodiment 12, 13, or 14, wherein the tapering of the at least a portion of the container is at least 60 degrees from vertical.

16. A system for transporting a composition according to any of embodiments 1-8, wherein the system comprises a conduit and gas to transport the composition through the conduit, optionally wherein the operating pressure of the system is about 5-105 psia, and optionally wherein the gas is air or an inert gas.

EXAMPLES

The present disclosure is further exemplified in the following Examples. It should be understood that these Examples, while indicating certain preferred aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

Example 1

Granular Alpha-Glucan Preparations with High Water Content

This Example describes preparing granular alpha-glucan compositions with high water content. In particular, granulated alpha-1,3-glucan samples were produced with a solids content of about 25 or 40 wt % (i.e., with about 75 or 60 wt % water, respectively).

A reaction was prepared comprising an amino acid-modified *S. salivarius* glucosyltransferase enzyme that produces (at a higher yield) insoluble alpha-1,3-glucan. Briefly, in a manner similar to what is described in U.S. Patent Appl. Publ. Nos. 2017/0166938, 2017/0002335, and 2018/0072998 (U.S. application Ser. No. 15/702,893) (all of which are incorporated herein by reference), for example, a glucan synthesis reaction was performed comprising water, sucrose, buffer and the amino acid-modified glucosyltransferase enzyme. Following the reaction, samples of the alpha-1,3-glucan product (insoluble, about 100% alpha-1,3 linkages, DPw of about 1000) were filtered, washed to remove most fructose and other residuals sugars, and squeezed to about 25 or 40 wt % solids using a filter press. The resulting glucan filter cakes contained about 75 or 60 wt % water, respectively, and about 0.4 wt % sugars. Each filter cake was chopped and then grated with a 6-mm grater into granules of about a ¼-inch average diameter. Despite having a high water content, both granulated alpha-1,3-glucan samples each had a powder-like appearance.

Example 2

Flowability of Granular Alpha-Glucan

This Example describes testing the flowability of the granulated alpha-1,3-glucan samples prepared in Example 1 above.

The flowability of bulk solid materials from silos, hoppers, and storage containers can have a significant effect on the ease with which the material can be retrieved from storage and delivered to a downstream process. Materials with poor flowability can require extraordinary efforts to promote discharge, and may completely block the discharge opening of storage vessels or refuse to discharge from flexible intermediate bulk containers (FIBC's, a.k.a. bulk bags or Super Sacks®). The mechanical properties (cohesive strength, bulk density and friction against the walls of process equipment) of a bulk solid will vary with the amount of compaction force applied to the specimen. Virtually all bulk materials gain cohesive strength with increasing compaction force, and many will gain further strength if held in a compacted state for an extended period of time. Bulk density increases with compaction force. The coefficient of friction against process equipment may be a constant value or may vary when compaction forces are increased.

Jenike (*Storage and Flow of Solids*, Bulletin 123 of the University of Utah Engineering Station, 1964), which is incorporated herein by reference, provides a methodology to convert measured values of cohesive strength, bulk density, and wall friction into estimates of the size of outlet necessary for free-flowing discharge of a bulk material from a hopper. Cohesive strength acts to impede flow while gravitational forces (from the bulk density) encourage flow. Wall friction determines flow pattern in the hopper. (For purposes of this discussion, for example, a hopper can be a rigid container having a cross section that converges toward an outlet opening. A traditional silo typically has a hopper section at the bottom and a straight-walled vertical section above it). Materials with poor flow properties will require larger hopper outlets—sometimes significantly so. The Jenike calculations require measurement of a bulk solid's properties at compaction stresses corresponding to the shape, size, and fill level of the hopper and any vertical extensions above it.

Jenike describes two possible types of flow patterns when a bulk solid discharges from a hopper. In "mass flow", the entire contents of the hopper are in motion whenever any material is withdrawn from the outlet. The bulk solid slides along the wall. In "funnel flow", friction of the bulk solids against the walls of the hopper prevents flow in that region. Instead, the bulk solid slides across itself down the central portion of the hopper. Due to the stresses imposed on the bulk solid by the flow pattern, mass flow hoppers will discharge from outlets that are appreciably smaller than those used in funnel flow hoppers. In a mass flow hopper, a flow blockage can occur if the outlet is too small, allowing arching by the bulk solid across the outlet's opening. In a funnel flow hopper, the flow pattern can lead to a different sort of blockage known as a rathole, or piping. A rathole is a self-supporting annular structure of bulk solid surrounding the outlet of the hopper. For both mass flow and funnel flow patterns, discharge will occur if the hopper outlet is sufficiently large to cause arches or ratholes (respectively) to collapse. However, for poor flowing solids, the required outlet dimensions can be so large as to be impractical. In practice, compared to preventing arching obstructions, preventing rathole obstructions requires using much larger hopper outlets. Thus, avoidance of ratholing is a key problem for particulate product developers and process designers.

The friction of a bulk solid against the walls of the hopper section, when combined with the inclination of the hopper walls, determines if the solids will slide along the walls (mass flow) or remain stagnant in the region of the walls (funnel flow). Mass flow is almost always desired, but may require hopper walls that are so steep as to make construction of the hopper impractical due to the vertical height required. Steep-walled hoppers are also impractical in mobile equipment and in retrofits of an existing bulk handling system that may have been designed around a more shallow design.

Jenike's procedures were originally intended as a means to design a bespoke hopper for a specific bulk solid, with the required hopper slope angles and outlet dimensions being the key calculated outcomes. However, when assessing the flowability of a bulk solid that may be used in a variety of hoppers, or when comparing two bulk solids' flowability to each other, it is convenient to determine the critical outlet diameter that would be required in a hypothetical silo of defined geometry and fill level. Hoppers with outlets larger than the critical diameter will discharge. This determination can be made for mass flow silos (in which an outlet diameter to overcome arching is calculated) or for funnel flow silos, for which a critical rathole diameter is calculated. In each case the units of outlet diameter are linear, with larger diameter-requiring outlets indicating proportionately worse flowability. Due to theoretical limitations in Jenike's methods, the testing and calculations may indicate rathole diameters in excess of the actual silo diameter. However, these results are still useful for comparative purposes. Indeed, in practice, it is known that if the critical rathole diameter approaches or exceeds the silo diameter, gravity flow may be impossible and large scale external flow promotion devices (e.g., vibrating discharge mechanisms) will be required.

The Jenike procedure traditionally utilizes values of cohesive strength and bulk density that are obtained from biaxial shear cells such as those described in ASTM standards D6128-16 or D6773-16, which are incorporated herein by reference. Results from these tests are subsequently interpreted using Jenike's methods. However, estimated values of critical rathole diameters can be more expeditiously obtained via the computer-controlled Johanson Hang-Up Indicizer® (Bell et al., *Bulk Solids Handling* 14:164-171; incorporated herein by reference). This device allows the user to enter a hypothetical silo diameter, and the system computes the required testing conditions and executes the test. The outcome is a critical rathole diameter for the hypothetical silo. In the Johanson device, a sample is confined in a shallow vertical cylindrical mold and then compressed with a downward stress corresponding to the load that would be encountered in the silo. After compression, a false bottom is removed from the central portion of the mold's bottom, leaving an annular ledge that supports the compacted sample. A probe is then inserted into the cylinder from the top. Downward motion of the probe forces a plug of compacted sample through the hole in the bottom of the mold. The force necessary to press the plug out of the bottom of the mold is measured. From the dimensions of the probe and the force measurement, the shear strength of the sample can be estimated and used to calculate the rathole diameter.

Flowability test results for granulated alpha-1,3-glucan at two different solids contents (40 or 25 wt %, as produced in Example 1 above, particles over 4 mm in size removed) are tabulated in Table 1 below. Test results were also tabulated for 10× powdered sugar (i.e., confectioners sugar) (Table 1), which is a convenient reference material with poor flow properties. Using a Johanson Hang-up Indicizer® with a 96-mL (maximum volume) test cell, each test was conducted at lab-scale at ambient temperature (~70° F.) with the respective sample briefly compacted and then tested ("instantaneous"), or with compaction forces applied for up to 960 minutes before testing. The testing conditions simulated a typical silo that is ten feet in diameter.

TABLE 1

Critical Rathole Diameters in 10-Foot Diameter Silo (Simulated) Containing Granulated Alpha-1,3-Glucan or Powdered Sugar

| Time of Compaction (minutes) | Critical Rathole Diameter (feet) | | |
| --- | --- | --- | --- |
| | Alpha-1,3-Glucan[a] 40 wt % solids | Alpha-1,3-Glucan[a] 25 wt % solids | 10X Sugar |
| 0.33 ("instantaneous") | 4.46 | 17.36 | 7.69 |
| 60 | 14.59 | 26.77 | 9.27 |
| 360 | 19.95 | 31.03 | not tested |
| 960 | 23.9 | 36.59 | not tested |

[a]Average particle diameter 4 mm or less. Loose bulk densities (prior to compression to mimic conditions at commercial-scale [e.g., hopper/silo]) of the 40 and 25 wt % material were about 37 and 32 pounds/cubic foot, respectively.

The data in Table 1 indicate that the 40 wt % solids form of granulated alpha-1,3-glucan has an initial ("instantaneous") flowability that would be considered poor, but is considerably better than powdered sugar. However, after storage of granulated 40 wt % alpha-1,3-glucan under load for 60 minutes or more, the critical rathole diameter increased dramatically, with additional time under load resulting in further increases in critical rathole diameter. Given the size of the ratholes that formed, the results in Table 1 overall suggest that a large outlet diameter (e.g., at least ~14 feet) would be necessary to permit continuous flow of granulated alpha-1,3-glucan from a commercial-size hopper or other large storage container.

The loose bulk densities of granulated 40 and 25 wt % alpha-1,3-glucan with particle sizes of 4 mm or less were measured to be about 37 and 32 pounds/cubic foot, respectively. The bulk densities of these 40- and 25-wt % materials following a compression of about 15-20, 65-70, 260-265, or 520-525 pounds/square foot were about 37, 38, 40, and 42, respectively, for the 40-wt % material, and about 33, 35, 38, and 42, respectively, for the 25-wt % material.

Based on the preceding test results (Table 1), severe difficulties in hopper discharge of 25-40 wt % solids glucan were expected. To accommodate the anticipated difficulties, tests at ambient temperature (~70° F.) were conducted with an aggressive hopper discharging device known as a Metalfab Posibin® (Metalfab Materials Handling Systems, Vernon, N.J.). The Posibin® is a portable hopper that is fitted with a full-diameter gyrating live bottom discharger. The entire hopper section is connected to a motor-driven eccentric vibrator, which can be turned on and off. The bin's inside diameter was slightly less than 36 inches, and its sidewall height was approximately 53 inches, providing about 35 cubic feet of working capacity. As is typical with gyrating live bottoms, there was a conical baffle plate inside the bin, a few inches above the bin outlet. Below the baffle was a ~10-inch (0.8-foot) diameter outlet. The hopper walls and the conical baffle plate had very shallow slopes, such that a funnel flow pattern would be expected if they were to discharge by gravity.

The Posibin® outlet was mechanically blocked and then the bin was loaded with loose granulated 40 wt % alpha-1, 3-glucan as prepared in Example 1 (no particles removed). Additional compaction stress (about 30 pounds/square foot) (i.e., additional to the compaction stress already existing by virtue of the weight of the glucan material itself) was applied by stacking concrete blocks on top of the loaded glucan, such that the total compaction stress in the bottom portion of the bin was about 150-200 pounds/square foot. The weights were applied for periods of up to several hours; the density of the granulated alpha-glucan from this compression was estimated to be about 40 pounds/cubic foot. After a designated time, the concrete weights were removed and the outlet was opened by removing its mechanical stop. In each of several trials, gravity discharge of the glucan from the bin commenced immediately upon opening the outlet, even though the vibrating discharge mechanism was never turned on. The glucan continued to flow from the bin until it was empty. This outcome was completely unexpected, since the 0.8-foot diameter outlet of the bin was much smaller than a 14-foot (or larger) outlet anticipated to be necessary for flow as suggested from the above lab-scale test results (Table 1). Similar Posibin® flow results were obtained using 40 wt % granulated alpha-1,3-glucan that had been prepared using a 3-mm grater (instead of a 6-mm grater).

In another test, the bin was re-loaded with 40 wt % granulated alpha-1,3-glucan and surcharged with weights, and left overnight (approximately 15 hours). The next morning, the mechanical block of the outlet was slid away, and the bin did not immediately start to discharge. The vibrator motor was energized for about two seconds, upon which flow commenced immediately, and continued (without further energizing of the vibrating discharge mechanism) until the bin was empty.

Gyrating live bottoms (discharge mechanisms) of hoppers should not be operated with the bin outlet closed, since the vibration can cause compaction of the bulk material and later discharging problems. As a simulation of the vibration that may occur in over-the-road transportation, the live bottom was used to vibrate a stagnant quantity of glucan in the bin. In this test, the Posibin® was filled with 40 wt % granulated alpha-1,3-glucan (but not surcharged with additional weight), after which the live bottom was operated for two continuous minutes and then shut off, all the while keeping the bin outlet mechanically blocked. After shutdown, the mechanical block was removed and the bin discharged completely without requiring the use of the vibrator to initiate flow. It is therefore contemplated that granulated glucan herein can be transported in containers without creating the flowability problems that typically affect other types of bulk material following their transport.

FIBC's (bulk bags) can be an economical method to transport up to about one ton of bulk material in a single package on a pallet. The bags have flexible walls and are hung from a frame for discharging through a bottom outlet spout. The bottom of the bag is nearly flat. The discharge flow pattern is therefore funnel flow. Products can be stagnant in bags for months awaiting use. It is inconvenient to mechanically vibrate or massage the bags to promote discharge, especially in a high-throughput operation. However, based on the lab-scale testing of flowability above (Table 1), difficulties in discharging bulk bags filled with granulated 25-40 wt % alpha-1,3-glucan was expected.

Two bulk bags with 19-inch (1.6-foot) diameter outlet spouts were tested. The bags had slightly conical bottoms, so that when they were lifted off the pallet the bottom formed a shallow hopper shape. The bags were filled with 40 wt % granulated alpha-1,3-glucan and then stored for 48 hours before discharging was tested. For discharging, the bags were suspended over a bin with a fork-lift truck. The spout of each bag was then untied, after which the bags discharged rapidly. The bags did not require prodding or any other form of agitation to promote flow of most of the granulated glucan out of the bags. After this emptying, a small amount of residual material was easily shaken out of the corners of each bag. This easy removal of the glucan by flow was unexpected for the reasons discussed above.

Example 3

Flowability of Granular Cationic Alpha-Glucan Ether

This Example describes testing the flowability of granulated, cationic ether-derivatized alpha-1,3-glucan.

Insoluble alpha-1,3-glucan (produced in a glucosyltransferase reaction similar to that described in Example 1 above) was ether-derivatized using 3-chloro-2-hydroxypropyl-trimethylammonium chloride. The resulting cationic ether derivative, trimethylammonium hydroxypropyl alpha-1,3-glucan, was aqueous-insoluble and had a degree of substitution (DoS) of less than 0.15. Insoluble cationic alpha-1, 3-glucan ether, which can have a DoS of less than 0.3, can be prepared, for example, by following the disclosure of U.S. Patent Appl. Publ. No. 2016/0311935 (incorporated herein by reference) and adjusting the ratio of alpha-1,3-glucan to cationic etherification agent accordingly.

Cationic alpha-1,3-glucan ether samples were washed with water and then granulated following a procedure similar to that described in Example 1 above. Each granulated sample had a powder-like appearance and a solids content of 38-40 wt %. The particle size was similar to that of the non-derivatized alpha-1,3-glucan particles produced in Example 1.

A flowability assessment was made for each of the granulated cationic alpha-1,3-glucan samples. Instead of using an automated Johanson Hang-Up Indicizer® as in Example 2, a portable test stand (van der Kraan and Scarlett, Proc. of PARTEC 95 and 3$^{rd}$ European Symposium—Storage and Flow of Particulate Solids, Nuremberg, 1995, pp. 57-68; incorporated herein by reference) was used to measure the shear strength of compressed glucan ether samples as a function of compression stress and the amount of time that the compaction stress was applied. As with the Johanson device, a downward stress was applied to a sample confined in a shallow cylindrical mold. However, with the portable tester, the downward stress was applied with iron weights corresponding to the stress that would be encountered in a silo or hopper of 4-feet in diameter. After a period of time, the weights were removed, as was the central portion of the bottom of the mold. The force (measured in grams-force) necessary to push a plug of compacted cationic glucan ether sample through the bottom of the mold was then measured. For similar test materials, the shear force measured in the portable tester correlates directly to the rathole index from the Johanson device.

Samples of granulated cationic glucan were tested for compaction times of 1, 60, 360, and 900 minutes. Replicate tests (usually five samples for each test duration) were conducted. As a comparison, the granulated non-derivatized alpha-1,3-glucan product that was tested in Example 2 was tested under the same conditions. Table 2 shows the average shear strength (as measured in grams-force) for each test.

TABLE 2

Force Necessary to Shear Compressed Samples

| Sample | Grams-Force Necessary to Shear Sample | | | |
|---|---|---|---|---|
| | 1 min.$^a$ | 60 min.$^a$ | 360 min.$^a$ | 900 min.$^a$ |
| Non-Derivatized Alpha-1,3-Glucan 40 wt % solids | <26 | <26 | not tested | <26 |
| Cationic Ether-Derivatized Alpha-1,3-Glucan 38-40 wt % solids | 77 | 361 | 321 | 655 |

$^a$Duration of sample compaction prior to application of force.

The portable tester cannot resolve shear forces less than the weight of the plug of sample within the fixture. In this case, the weight of the plug was approximately 26 grams. In testing the non-derivatized alpha-1,3-glucan, each sample fell from the bottom of the fixture when the central portion of the bottom of the mold was removed, and thus no force from the probe was required.

Table 2 indicates that the granulated cationic alpha-1,3-glucan ether samples had substantially higher shear strength than that of the granulated non-derivatized alpha-1,3-glucan samples after similar compaction times. As discussed in Example 2, the data in Table 1 would lead one to predict that granulated non-derivatized alpha-1,3-glucan would experience substantial ratholing problems in handling. Consequently, one would expect even more severe ratholing problems when handling granulated cationic alpha-1,3-glucan. Surprisingly, however, it was found that cationic alpha-1,3-glucan ether could be processed through a sequence of handling and processing devices without appreciable difficulty. These devices included belt conveyors, screw conveyors, screw feeders and milling machines. In one portion of the processing sequence, cationic alpha-1,3-glucan ether was loaded into a pyramid-shaped hopper that was 3-feet× 3-feet at the top and 27 inches tall, with a rectangular outlet that was 7 inches wide by 12 inches long. A hopper with this shape would have a funnel flow discharge pattern. A standard screw conveyor below the outlet discharged the hopper. Very little intervention was necessary to overcome any ratholing of cationic alpha-1,3-glucan ether in this hopper, even though the shear strength data (Table 2) predicted that there should have been serious flow problems.

What is claimed is:

1. Particles with an average size of about 0.1-10 mm, wherein said particles comprise at least
   (i) about 50%-90% by weight water or an aqueous solution, and
   (ii) about 10%-50% by weight insoluble alpha-glucan or an insoluble cationic ether of said insoluble alpha-glucan,
   wherein the insoluble alpha-glucan comprises at least 50% alpha-1,3-glycosidic linkages and has a weight-average degree of polymerization (DPw) of at least 100, and wherein the particles are powder-like.

2. The particles of claim 1, wherein the insoluble alpha-glucan has at least 80% alpha-1,3-glycosidic linkages.

3. The particles of claim 1, wherein the particles comprise about 30%-45% by weight of said insoluble alpha-glucan or insoluble cationic ether thereof.

4. The particles of claim 1, wherein the insoluble alpha-glucan has at least 90% alpha-1,3-glycosidic linkages.

5. The particles of claim 1, wherein the insoluble alpha-glucan is enzymatically produced in a reaction composition comprising at least water, sucrose and a glucosyltransferase enzyme that synthesizes insoluble alpha-glucan.

6. The particles of claim 1, wherein the particles are produced by contacting a first composition with a particle-forming device, wherein said first composition comprises at least (i) about 50%-90% by weight water or an aqueous solution, and (ii) about 10%-50% by weight of said insoluble alpha-glucan.

7. The particles of claim 6, wherein the first composition is a cake of the insoluble alpha-glucan.

8. The particles of claim 1, wherein the particles comprise said insoluble alpha-glucan.

9. A method of preparing a particles of claim 1, said method comprising:
   (a) providing a first composition comprising at least (i) about 50%-90% by weight water or an aqueous solution, and (ii) about 10%-50% by weight of said insoluble alpha-glucan or said insoluble cationic ether of said insoluble alpha-glucan, and
   (b) providing particles of the first composition with an average size of about 0.1-10 mm.

10. The method of claim 9, wherein the first composition is a cake of the insoluble alpha-glucan.

11. The method of claim 9, wherein step (b) comprises contacting the first composition with a particle-forming device, optionally wherein the particle-forming device comprises a plurality of 0.1-mm to 10-mm passages through which the first composition is forcibly transited, and optionally further wherein the particle-forming device comprises a screen.

12. The particles of claim 3, wherein the particles comprise said insoluble alpha-glucan.

13. The particles of claim 1, wherein the particles comprise said insoluble cationic ether of said insoluble alpha-glucan.

14. The particles of claim 1, wherein the particles are continuously flowable.

15. The particles of claim 1, wherein the particles comprise less than 0.5% by weight any other substance aside from those of (i) and (ii).

16. The particles of claim 15, wherein said other substance comprises a filler.

17. The particles of claim 16, wherein said filler comprises wood or pulp.

18. The particles of claim 15, wherein said other substance comprises a plasticizer.

19. The particles of claim 18, wherein said plasticizer comprises glycerol.

* * * * *